United States Patent
McCormick

(10) Patent No.: US 9,949,744 B2
(45) Date of Patent: Apr. 24, 2018

(54) IMPLANT SUITABLE FOR CALCANEAL OSTEOTOMY

(71) Applicant: Wright Medical Technology, Inc., Arlington, TN (US)

(72) Inventor: Daniel McCormick, Bartlett, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 64 days.

(21) Appl. No.: 14/011,244

(22) Filed: Aug. 27, 2013

(65) Prior Publication Data

US 2014/0066995 A1   Mar. 6, 2014

Related U.S. Application Data

(60) Provisional application No. 61/695,162, filed on Aug. 30, 2012.

(51) Int. Cl.
| | |
|---|---|
| *A61B 17/80* | (2006.01) |
| *A61B 17/17* | (2006.01) |
| *A61B 17/16* | (2006.01) |
| *A61B 17/72* | (2006.01) |

(52) U.S. Cl.
CPC ........ *A61B 17/1728* (2013.01); *A61B 17/809* (2013.01); *A61B 17/8052* (2013.01); *A61B 17/8061* (2013.01); *A61B 17/8095* (2013.01); *A61B 17/1682* (2013.01); *A61B 17/1686* (2013.01); *A61B 17/7291* (2013.01)

(58) Field of Classification Search
CPC .............. A61B 17/809; A61B 17/8052; A61B 17/8095; A61B 17/8061; A61B 17/1728; A61B 17/1682; A61B 17/1686; A61B 17/7291

USPC .................................................. 606/308, 297
See application file for complete search history.

(56) References Cited

U.S. PATENT DOCUMENTS

| | | | | |
|---|---|---|---|---|
| 3,486,500 | A | * | 12/1969 | Ball Kenneth et al. ........ 606/67 |
| 4,120,298 | A | * | 10/1978 | Fixel ...................... A61B 17/74 |
| | | | | 606/70 |
| 4,651,724 | A | | 3/1987 | Berentey et al. |
| 5,047,059 | A | * | 9/1991 | Saffar ........................ 623/21.15 |

(Continued)

FOREIGN PATENT DOCUMENTS

| | | |
|---|---|---|
| DE | 26 02 900 A1 | 7/1977 |
| EP | 1952776 A1 | 8/2008 |

(Continued)

OTHER PUBLICATIONS

International Search Report and Written Opinion issued for International Patent Application No. PCT/US2013/056942, Mar. 20, 2015, 11 pages.

(Continued)

*Primary Examiner* — Tatiana Nobrega
*Assistant Examiner* — Marcela I Shirsat
(74) *Attorney, Agent, or Firm* — Duane Morris LLP

(57) ABSTRACT

An implant comprises an elongated plate having a first major face and at least one locking screw hole, to receive a locking fastener oriented normal to the major face. The elongated plate has a wall with a flat surface normal to the first major face. A non-locking screw hole is located between the locking screw hole and the wall. The non-locking screw hole is configured to receive a non-locking fastener oriented at an acute angle relative to the locking fastener.

12 Claims, 15 Drawing Sheets

(56) References Cited

U.S. PATENT DOCUMENTS

| | | | |
|---|---|---|---|
| 5,662,655 A | 9/1997 | Laboureau et al. | |
| 6,045,552 A | 4/2000 | Zucherman et al. | |
| 6,190,389 B1 * | 2/2001 | Wellisz | A61B 17/688 606/281 |
| 6,302,884 B1 * | 10/2001 | Wellisz et al. | 606/86 B |
| 6,336,927 B2 | 1/2002 | Rogozinski | |
| 8,057,520 B2 | 11/2011 | Ducharme et al. | |
| 2005/0171544 A1 | 8/2005 | Falkner, Jr. | |
| 2006/0004361 A1 | 1/2006 | Hayeck et al. | |
| 2008/0015593 A1 | 1/2008 | Pfefferle et al. | |
| 2008/0039851 A1 | 2/2008 | Schulz et al. | |
| 2008/0082102 A1 | 4/2008 | Bruecker et al. | |
| 2009/0012570 A1 | 1/2009 | Zhang et al. | |
| 2009/0036931 A1 | 2/2009 | Pech et al. | |
| 2009/0088768 A1 | 4/2009 | Grant et al. | |
| 2010/0100138 A1 | 4/2010 | Reynolds et al. | |
| 2010/0198262 A1 | 8/2010 | McKinley | |
| 2010/0274293 A1 | 10/2010 | Terrill et al. | |
| 2011/0009866 A1 | 1/2011 | Johnson et al. | |
| 2011/0144644 A1 * | 6/2011 | Prandi et al. | 606/62 |
| 2011/0306977 A1 * | 12/2011 | Michel | A61B 17/15 606/71 |
| 2012/0209334 A1 | 8/2012 | Lewis et al. | |

FOREIGN PATENT DOCUMENTS

| | | |
|---|---|---|
| JP | 2010-538683 A1 | 12/2010 |
| JP | 2015-529135 A | 10/2015 |
| WO | 2008/149223 A2 | 12/2008 |
| WO | 2010/061410 A1 | 6/2010 |
| WO | 2015/026375 A2 | 2/2015 |

OTHER PUBLICATIONS

Partial Supplementary European Search Report issued in connection with corresponding European Application No. 13891887.5, Mar. 2, 2016, 5 pages.

First Office Action issued in connection with corresponding Chinese Application No. 201380045065.1, Jul. 29, 2016, 9 pages.

First Office Action issued for corresponding Japanese patent application No. 2016-226776, dated Aug. 29, 2017, 5 pages.

Extended European Search Report issued in connection with European patent application No. 17175083.9, dated Sep. 29, 2017, 7 pages.

* cited by examiner

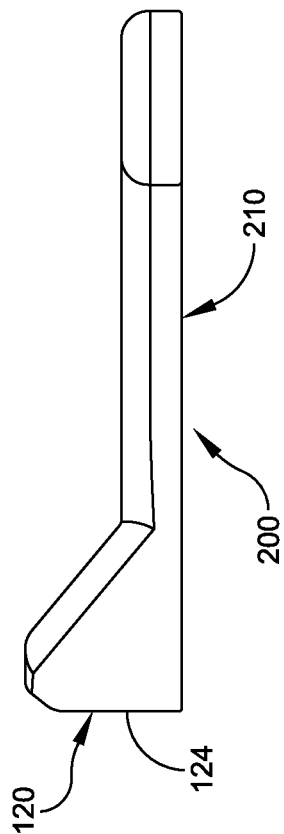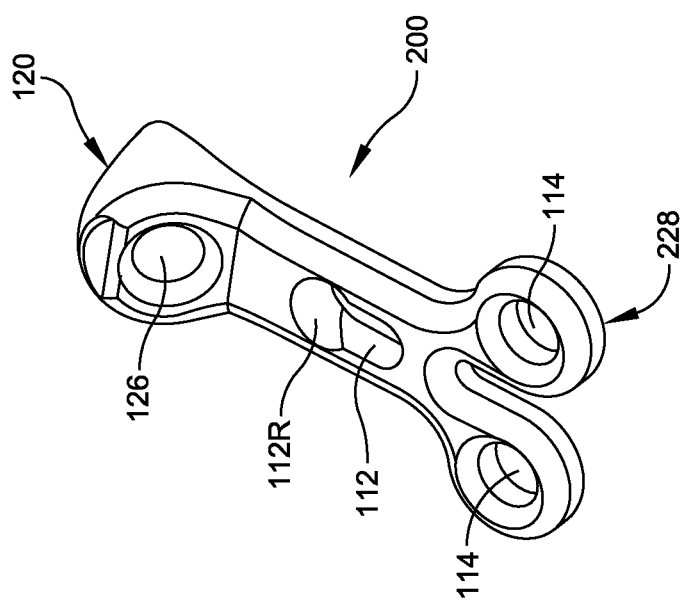
FIG. 4B
FIG. 4A

IMPLANT SUITABLE FOR CALCANEAL OSTEOTOMY

FIELD

This disclosure relates to an implant for an osteotomy, and tools for inserting an implant.

BACKGROUND

A calcaneal osteotomy is a form of surgery for correction of severe hind foot misalignment. During the procedure, the heel bone (calcaneus) is cut, and the tuberosity is moved medially toward the inside or laterally toward the outside, depending upon the direction of the misalignment that is to be corrected. For example, if the patient has flat feet, the heel may be offset medially to shift the hind foot toward the inside to improve the weight distribution on the foot. On the other hand, if the patient has a high arched foot the calcaneal osteotomy may be performed to shift the hind foot laterally, to improve stability and reduce risk of sprain. This procedure has been performed by cutting the bone, moving the tuberosity medially or laterally, and driving screws through the tuberosity into the anterior calcaneus. Some of the challenges associated with this approach are determining the amount of intra-operative offset that is achievable, the capability of fluoroscopy techniques for targeting and placing of screws, and post-placement screw head prominence.

Implants are known for insertion during calcaneal osteotomy. For example, the assignee of this patent application, Wright Medical Technologies, has developed the DARCO® DPS plate, which provides support. This implant includes an anterior plate, a posterior plate, and an offset segment connecting the anterior and posterior plates. The DARCO® DPS plate is available with different amounts of offset between the anterior and posterior plates.

U.S. Patent Application Publication No. 2011/0009866 describes an osteotomy plate having a top side and a bottom side, with a first end and a second end aligned along a longitudinal axis and joined by a middle section. The first end includes a cutting edge having a chamfer of between about 5° and 30°. As a screw hole in the first end forms an angle of from about 10° to about 45° with respect to the longitudinal axis of the plate. The screw hole is not threaded, but does include an arcuate shroud on the top side of the plate. The second end has a locking hole which includes internal threads. The first hole and the second hole are aligned along the longitudinal axis. One or more of additional screw holes, compression holes, fenestrations or guide wire holes are provided.

Improved osteotomy plates are desired.

SUMMARY

In some embodiments, an implant comprises an elongated plate having a first major face and at least one locking screw hole to receive a locking fastener oriented normal to the major face. The elongated plate has a wall having a flat surface normal to the first major face. A non-locking screw hole is located between the locking screw hole and the wall. The non-locking screw hole is configured to receive a non-locking fastener oriented at an acute angle relative to the locking fastener.

In some embodiments, an implant may comprise an elongated plate having a first major face and at least one locking screw hole normal to the major face, to receive a locking fastener. The elongated plate has a non-locking screw hole configured to receive a non-locking fastener oriented at an acute angle relative to the locking fastener. At least one insertion member extends in an anterior direction, away from the locking screw hole, the at least one insertion member having an edge with barbs.

A method is also provided, which in some embodiments, comprises: (a) fastening an implant to a first portion of a bone, so that a face of the implant abuts the bone, the implant having a hole configured to receive a fastener oriented at an obtuse angle relative to the face, the implant having a flat surface normal to the face; (b) cutting the bone along a plane of the flat surface, so as to separate a second portion of the bone from the first portion of the bone; (c) offsetting the second portions of the bone relative to the first portion of the bone, such that the flat surface of the implant abuts the second portion of the bone; and (d) fastening the implant to the second portion of the bone using the fastener.

BRIEF DESCRIPTION OF THE DRAWINGS

FIG. 4A is a perspective view of the implant of FIG. 4.

FIG. 4B is a side view of the implant of FIG. 4.

DETAILED DESCRIPTION

Figure 1:
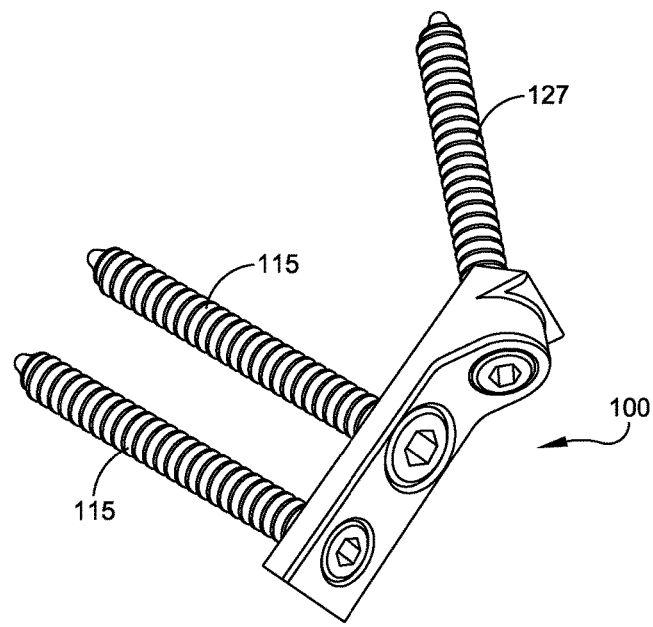
FIG. 1 is a perspective view of an embodiment of an implant, with insertion screws.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," "anterior," "posterior," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. In the various drawings, like reference numerals indicate like items, unless expressly indicated otherwise.

Figure 2:
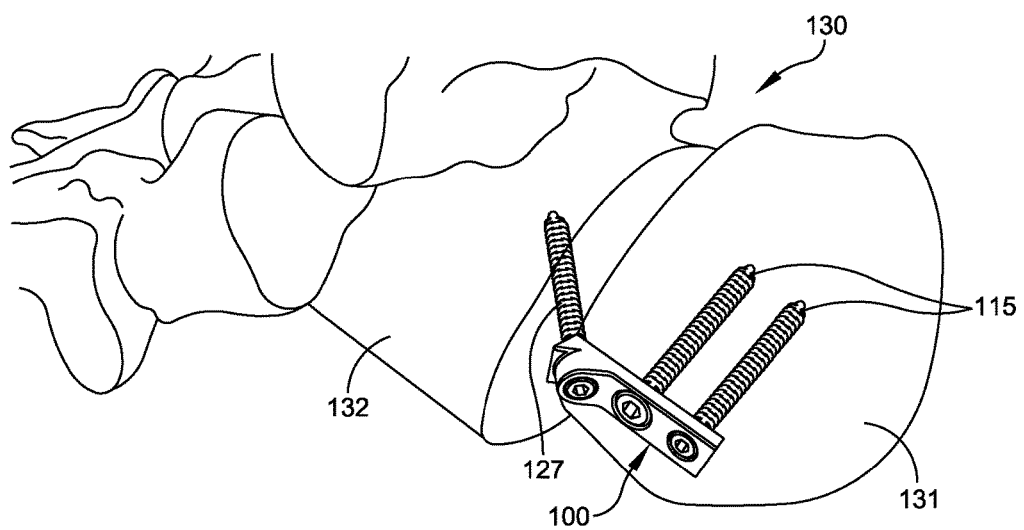
FIG. 2 is a diagram of the implant of FIG. 1, inserted in a calcaneus.
Figure 3:
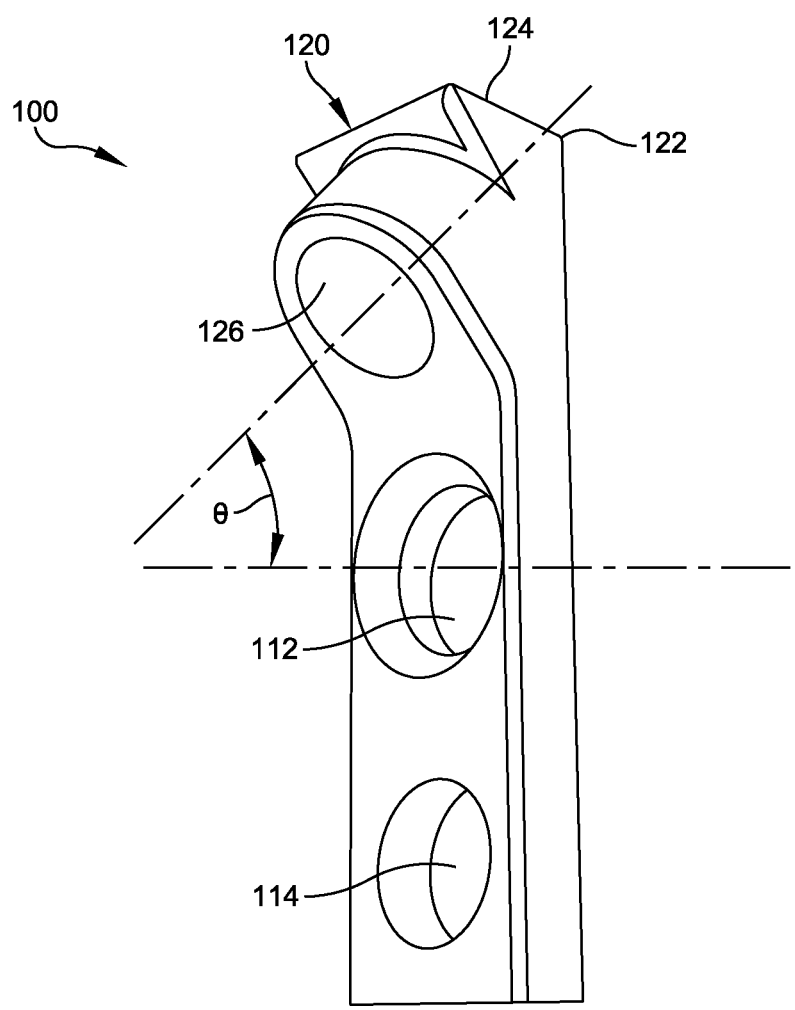
FIG. 3 is a perspective view of the implant of FIG. 1.
Figure 3A:
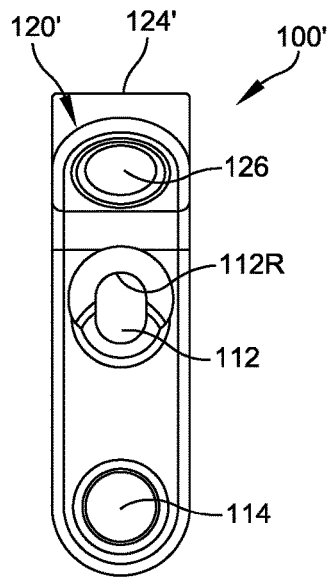
FIG. 3A is a top plan view of a variation of the implant of FIG. 3.
Figure 3B:
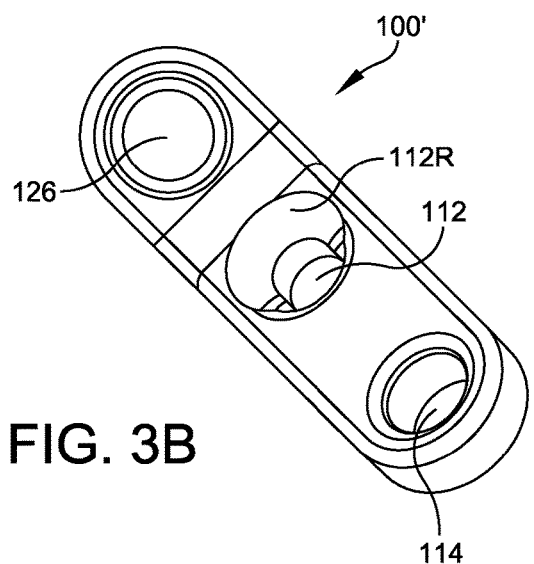
FIG. 3B is a 45 degree plan view looking directly into the non-locking fastener hole of the implant of FIG. 3A.
Figure 3C:
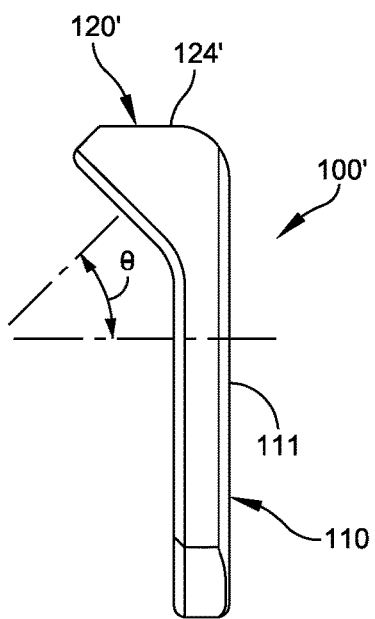
FIG. 3C is a side elevation view of the implant of FIG. 3A.
Figure 3D:
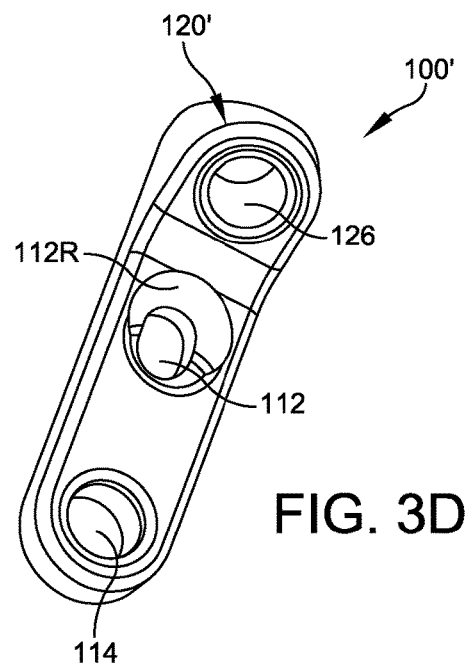
FIG. 3D is a perspective view of the implant of FIG. 3A.

FIGS. 1-3 show a first embodiment of an implant 100 for an osteotomy, such as a calcaneal osteotomy. The implant 100 allows polyaxial screw placement, with both locking and non-locking screw holes. The implant 100 includes an elongated plate 110 having a first major face 111 and at least one locking screw hole 114 that is defined normal to the major face 111, to receive a locking fastener 115. In some embodiments, the locking screw hole 114 is located at an end of the implant 100, distal from the joint line where the calcaneus 130 is cut, and the tuberosity 131 is to be rejoined to the anterior calcaneus 132. The locking screw hole 114 has a female thread for locking the plate 100 against the lateral or medial side of the tuberosity 131 and tightening the implant 100 down against the tuberosity.

The elongated plate 110 includes a non-locking screw hole 126 configured to receive a non-locking fastener 127 at an end of implant 100 opposite locking screw hole 114. The non-locking screw hole 126 is oriented at an acute angle θ relative to the locking fastener and locking screw hole 114. The implant 100 includes an abutting end 120 with a wall having a flat surface 124, which may be normal to the first major face 111. The non-locking screw hole 126 penetrates the flat surface 124 of the wall. The non-locking screw hole 126 is oriented at an angle θ of about 30 degrees to about 60 degrees from the locking screw hole 114. In some embodiments, the non-locking screw hole 126 is oriented at an angle θ of about 40 degrees to about 50 degrees from the locking screw hole 114. In some embodiments, the non-locking screw hole 126 is oriented at an angle θ of about 45 degrees from the locking screw hole 112.

Referring to FIG. 2, implant 100 may have the first major face 111 of elongated plate 110 affixed to a lateral or medial side of the tuberosity 131 of the calcaneus 130, with the normal flat surface 124 abutting the posterior facing cut surface of the anterior calcaneus 132. In some embodiments, the implant is affixed to the tuberosity 131 such that the flat anterior surface 124 of implant 100 is recessed, about 0.127 mm to 0.381 mm in the posterior direction relative to the cut surface of the tuberosity 131. Thus, when the implant plate 100 is fastened to the anterior calcaneus 132, and the fasteners 115, 127 are tightened, there is a 0.127 mm to 0.381 mm translation of the implant plate 100 resulting in advantageous compression of the calcaneus against the tuberosity. When the non-locking screw 127 is inserted through the hole 126 and tightened, the anterior calcaneus 132 is pulled towards the tuberosity 131 by up to 0.127 to 0.381 mm, until the anterior surface 124 of the implant 100 abuts the cut surface of the anterior calcaneus 132. This provides compression of the two abutting cut surfaces of the tuberosity 131 and anterior calcaneus 132, enhancing rotational stability about the anatomical axes resulting in solid fixation. Since face 124 abuts the cut surface of the anterior calcaneus 132, there is no requirement to drive the implant 100 into the anterior calcaneus 132 before inserting either of the fasteners 115, 127. This arrangement simplifies the surgical procedure and reduces the duration of the surgery. Also, of the implant 100 fitting in a corner formed between the lateral (or medial) surface of the tuberosity 131 and the cut surface of the anterior calcaneus 132, the implant 100 does not extend along the lateral (or medial) surface of the anterior calcaneus beyond the cut line. In some embodiments, elongated plate 110 further comprises a compression slot 112 between locking screw hole 114 and non-locking screw hole 126. The compression slot 112 has a ramped surface 112R on its anterior side, toward flat anterior surface 124. When a ramped compression screw is inserted into compression slot 112, subsequent tightening of the screw causes implant 100 to translate in the anterior direction away from the locking screw hole 114.

The implant 100 is affixed to the calcaneus 130 by first inserting locking screw 115 though locking screw hole 114 distal from the joint-line (where the calcaneus has been cut). A compression screw is then inserted in compression slot 112, which forces implant 100 to translate in the anterior direction away from locking screw hole 114 and compress the joint-line between the tuberosity 131 and anterior calcaneus 132. Then, a non-locking screw is inserted through the angled non-locking screw hole 126. The head of this non-locking screw hole 126 is on the same side of the joint-line as compression slot 112, and fixes implant 100 in its compressed state. The screw advances into the anterior calcaneus 132 on the opposite side of the joint line.

In some embodiments, the locking screw is first inserted into hole 114 to affix the posterior portion of implant 100 to tuberosity 131. Then, the bone of the calcaneus 130 is cut about 0.127 to 0.381 mm beyond the flat anterior surface 124 of implant 100. In other embodiments, a cutting guide is attached to the implant to guide the location of the cut in the bone along a plane that is substantially parallel to anterior flat face 124 of implant 100. Once in this position, the guide may be removed from implant 100. In further embodiments, a second tool is attached to the implant for drilling the non-locking screw hole 126 so that it is sized to receive the non-locking screw. This tool may include a drill guide which is inserted into non-locking screw hole 126 for correctly aligning non-locking screw 126. In some embodiments, this tool has an offset medial displacement shelf, which is temporarily fixed to the lateral or medial surface of the anterior calcaneus 132 so as to positively locate bottom surface 111 of implant 100 in the medial-lateral direction relative to the anterior calcaneus. This allows control of the offset between the anterior calcaneus 132 and tuberosity 131. Because flat face 124 of implant 100 abuts the cut surface of the anterior calcaneus 132 and is directly fastened to the cut surface, a single size of implant 100 may be used for osteotomies involving a variety of different offsets between the tuberosity and anterior calcaneus. In other embodiments, the tool provides the capability of continuously varying the position of the medial displacement shelf. This arrangement allows the surgeon to select the size of the offset, which can be varied throughout the range of offsets used for calcaneal osteotomies.

In many embodiments, the offset between bottom surface 111 of implant 100 and the lateral/medial surface of the anterior calcaneus 132 is determined using a fixed offset insertion tool. A set of such tools may be provided to the surgeon, with each tool having a respective offset. In some embodiments, the implant is formed of a biocompatible material, such as a titanium alloy or stainless steel of the type known for use in surgical procedures. In some embodiments (e.g., FIG. 1), implant 100 defines a single row of screw holes 114, 112, 126, and has a width sufficient to secure implant 100 with a single row of holes. In other embodiments, the implant defines additional holes, and may be wider, to improve stability.

In the various drawings referred to in the following description of alternative embodiments, the implant plate may be shown alone or positioned on the calcaneus without fasteners, such as screws. This is solely to provide a clear and simple illustration of the implant plates. One of ordinary skill would understand that each of the implants is intended for use with at least one anterior fastener and at least one posterior fastener. Some of the embodiments are configured with at least one compression slot and are intended for use with at least one compression screw.

FIGS. 3A to 3D show an implant 100', which illustrates a variation of the implant shown in FIG. 3, in which the square corners of the abutting end 120 are replaced by smooth edges in abutting end 120'. The posterior portion of implant 100' includes the same locking fastener hole 114 and compression hole 112 (with ramped surface 112R), and non-locking fastener hole 126 as in implant 100, and descriptions of these like features are not repeated here. The structure of implant 100' also provides a flat abutting surface 124' for interfacing with the cut surface of the anterior calcaneus 132, however, the corners of abutting end 120' are smooth rounded curves. The elimination of square cornered edges on implant 100' may be more comfortable for some patients.

Figure 4:
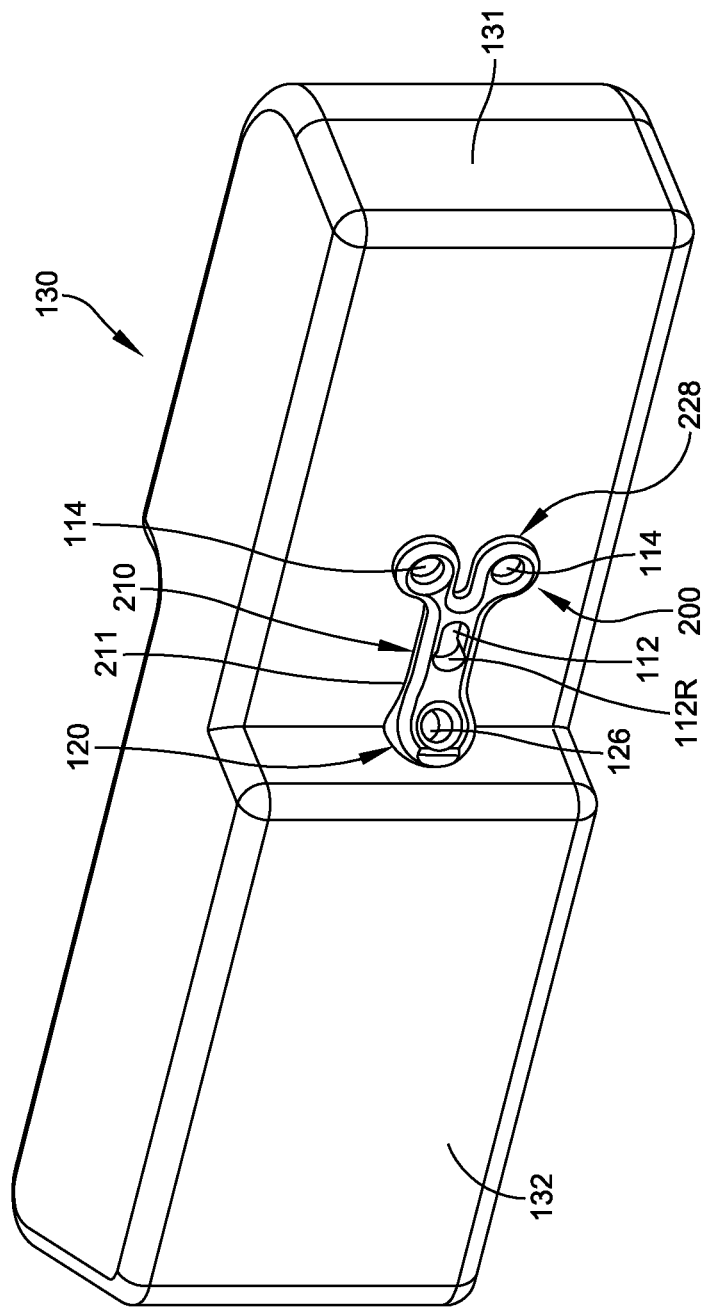
FIG. 4 is a perspective view of a second embodiment of an implant, inserted in the calcaneus.

FIGS. 4, 4A and 4B show an embodiment of an implant 200 having a generally T-shaped configuration. Note that in FIG. 4, the tuberosity 131 and anterior calcaneus 132 are only shown in outline, and the details of the bones (shown in FIG. 2) are omitted for ease of viewing the implant. The implant 200 of FIG. 4 can be used for osteotomy involving the same bone as the implant shown in FIG. 2. The same is also true of the views of the calcaneus 130 in FIGS. 5, 6, 9B and 9C. More particularly, anterior portion 220 of implant 200 may be the same as described above with reference to anterior portion 120 of implant 100 shown in FIG. 3. This includes a flat anterior surface 124, a non-locking screw hole 126, and a compression slot 112, which may all be the same as described above with reference to implant 100 of FIG. 3, and descriptions thereof are not repeated here. The anterior portion of plate 210 may also be the same as the anterior portion of plate 110 of implant 100.

Implant 200 has a posterior portion 228 including a plurality of posterior locking screw holes 114 which may be arranged symmetrically about a longitudinal axis of implant 200. Two posterior locking screws may be inserted into holes 114 so as to provide additional stability and resistance to twisting of implant 200. Implant 200 is affixed to the calcaneus 130 by first inserting the locking screws (not shown) through locking screw holes 114 distal from the joint-line. A compression screw is then inserted into compression slot 112, which forces implant 200 to translate toward the anterior direction and away from locking screw holes 114 thereby compressing the joint-line between the tuberosity 131 and anterior calcaneus 132. Then, a non-locking screw is inserted through the angled non-locking screw hole 126.

Figure 5:
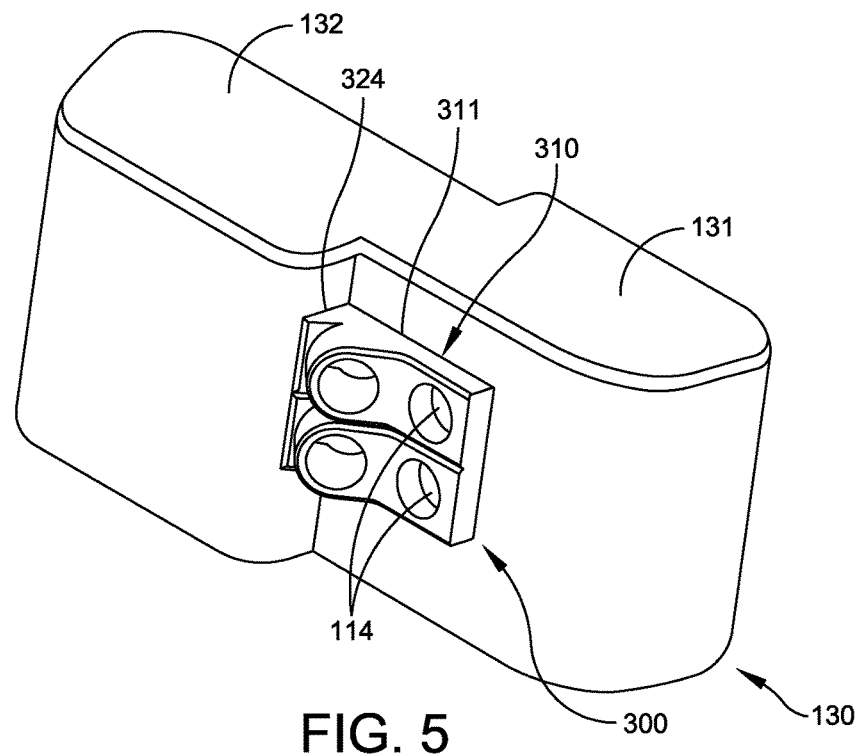
FIG. 5 is a perspective view of a third embodiment of an implant, inserted in the calcaneus.

FIG. 5 shows an embodiment of the invention utilizing an implant 300 having two rows of fastener holes 114, 126. Implant 300 includes a wider flat anterior surface 324, having two non-locking screw holes 126, which may be the same as described above with reference to implant 100 of FIG. 3, and descriptions thereof are not repeated here. Implant 300 also has two posterior locking screw holes 114, which may be the same as described above with reference to implant 100 of FIG. 3. Two non-locking screws are inserted into non-locking screw holes 126 and two posterior locking screws are inserted into holes 114 to provide additional stability and resist twisting of implant 300. The implant 300 is affixed to the calcaneus 130 by first inserting locking screws 115 (FIG. 1) through locking screw holes 114 distal from the joint-line. Then, the non-locking screws are inserted through the angled non-locking screw hole 126.

Figure 6:
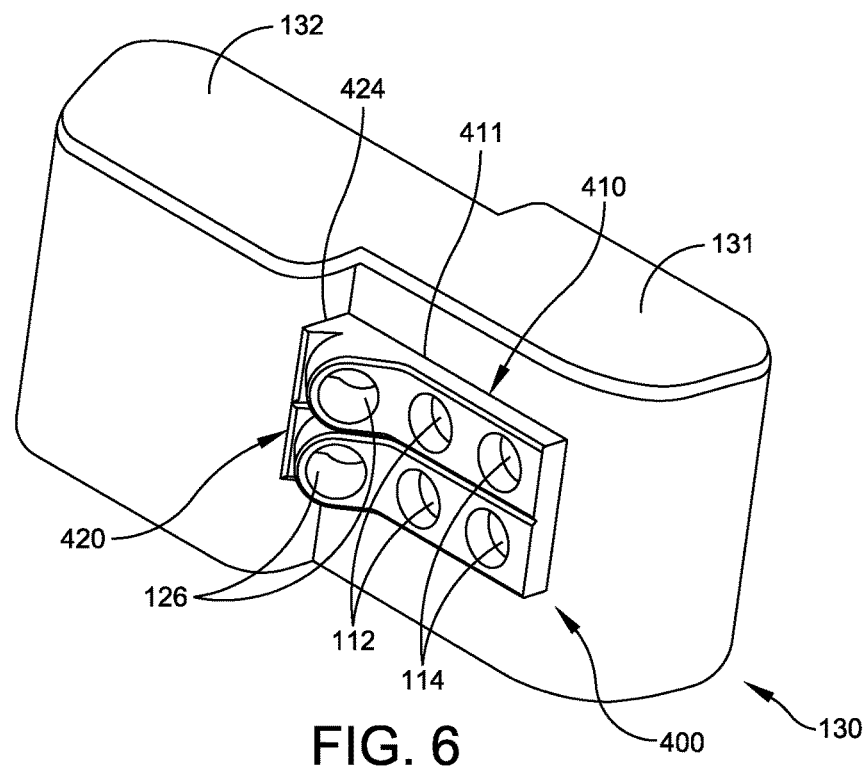
FIG. 6 is a perspective view of a fourth embodiment of an implant, inserted in the calcaneus.

FIG. 6 shows an embodiment of the invention utilizing an implant 400 having two rows of fastener holes 114, 126. Implant 400 includes an anterior portion 410 having a wider flat anterior surface 324, and two non-locking screw holes 126, which may be the same as described above with reference to implant 300 of FIG. 5, and descriptions thereof are not repeated here. Implant 400 also has two posterior locking screw holes 114, which may be the same as described above with reference to implant 300 of FIG. 5. In addition, implant 400 includes two compression screw slots 112 for receiving compression screws and positioning the implant 400. Implant 300 is affixed to the calcaneus 130 by first inserting the locking screws (not shown) through locking screw holes 114 distal from the joint-line. Then, the compression screws are inserted in compression screw holes 112, and the non-locking screws are inserted through angled non-locking screw hole 126.

Figure 7:
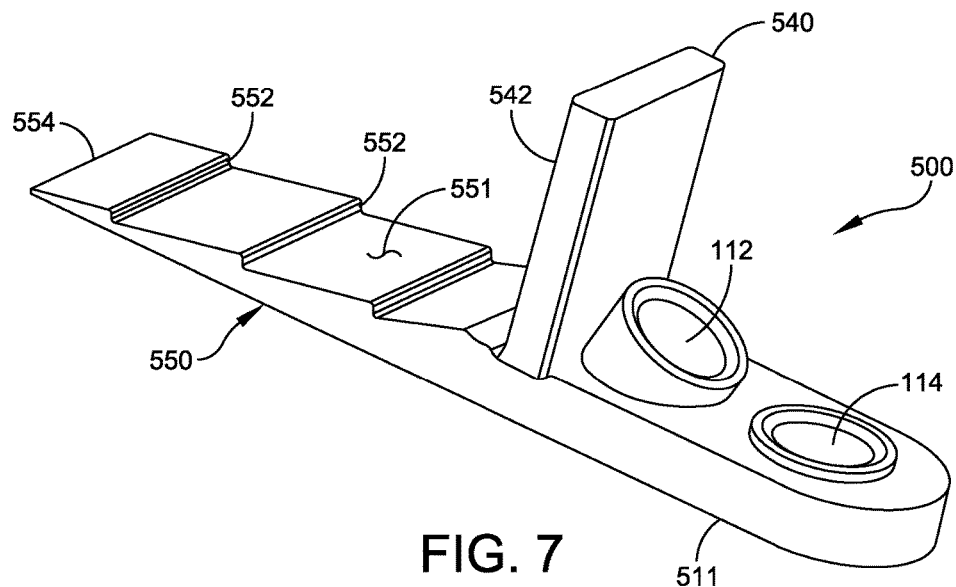
FIG. 7 is a perspective view of a fifth embodiment of an implant.

FIG. 7 shows another embodiment of the invention utilizing an implant 500, having at least one insertion member 550 that extends beyond a wall 540 in an anterior direction, away from an elongated plate 510. The at least one insertion member 550 has a top face 551 with ridges or barbs 552. The top face 551 confronts face 511, which abuts the lateral or medial surface of the tuberosity 131. The thickness of the insertion member generally decreases toward an anterior end 554 of insertion member 550. The insertion member 550 with ridges or barbs 552 is configured to be driven into the cut surface of the anterior calcaneus 132. Ridges or barbs 552 allow implant 500 to provide additional resistance to pulling out from the anterior calcaneus 132. Wall 540 is configured so that anterior surface 542 of wall 540 abuts the cut surface of the anterior calcaneus 132 when implant 500 is driven into the bone 132 to a desired depth. Wall 540 also helps prevent the surgeon from inadvertently driving implant 500 too far into the bone. In some embodiments, wall 540 includes a fillet to provide additional strength to implant 500.

Figure 8:
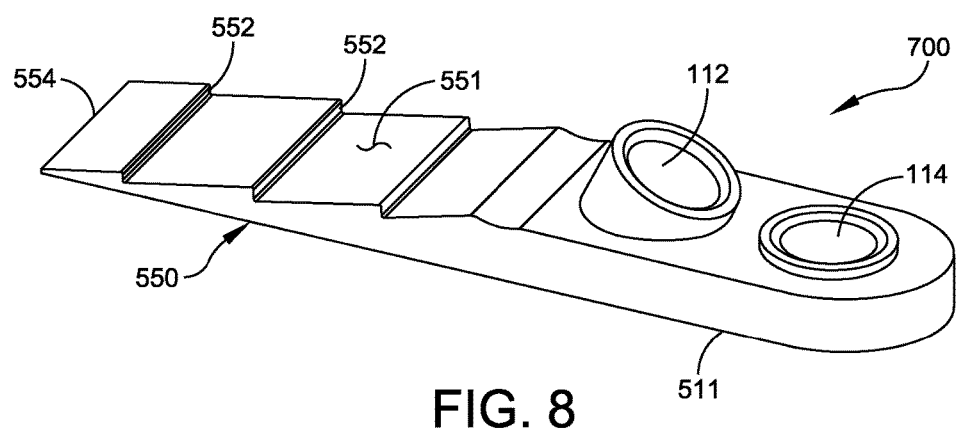
FIG. 8 is a perspective view of a sixth embodiment of an implant.

FIG. 8 shows another embodiment of the invention utilizing an implant 700, which is similar to the implant 500 of FIG. 7, except that implant 700 does not include wall 540 of implant 500. Implant 700 has at least one insertion member 550 extending beyond the anterior non-locking screw hole 112 in an anterior direction, away from the elongated plate 510. The at least one insertion member 550 has a top face 551 with ridges or barbs 552. The top face 551 is opposite the face 511, which abuts the lateral or medial surface of the tuberosity 131. The thickness of the insertion member generally decreases toward anterior end 554 of insertion member 550. Insertion member 550 with ridges or barbs 552 is configured to be driven into a cut surface of the anterior calcaneus 132. The ridges or barbs 552 give the implant 500 additional resistance to pulling out from the anterior calcaneus 132.

Figure 9A:
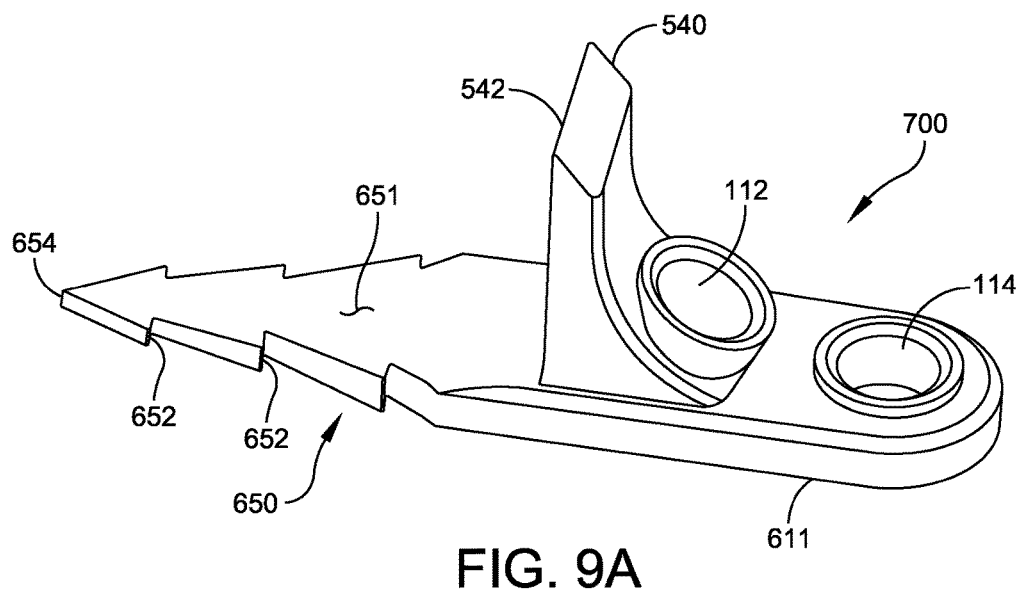
FIG. 9A is a perspective view of a seventh embodiment of an implant.

FIG. 9A shows another embodiment of the invention utilizing an implant 600, having at least one insertion member 650 extending beyond wall 540 in an anterior direction, away from the elongated plate 510. The at least one insertion member 650 has ridges or barbs 652 on the side edges of the insertion member 650. The top face 651 of the insertion member 650 is a ramped planar surface. The thickness of insertion member 650 generally decreases toward anterior end 654 of insertion member 650. The width of insertion member 650 also gradually decreases toward anterior end. The insertion member 650 with ridges or barbs 652 is configured to be driven into the cut surface of the anterior calcaneus 132. The ridges or barbs 652 give the implant 600 additional resistance to pulling out from the anterior calcaneus 132. The posterior portion of implant 600, extending from wall 540 to locking screw hole 114 can be the same as discussed above with reference to implant 500, and descriptions of the individual structures are not repeated here.

Figure 9B:
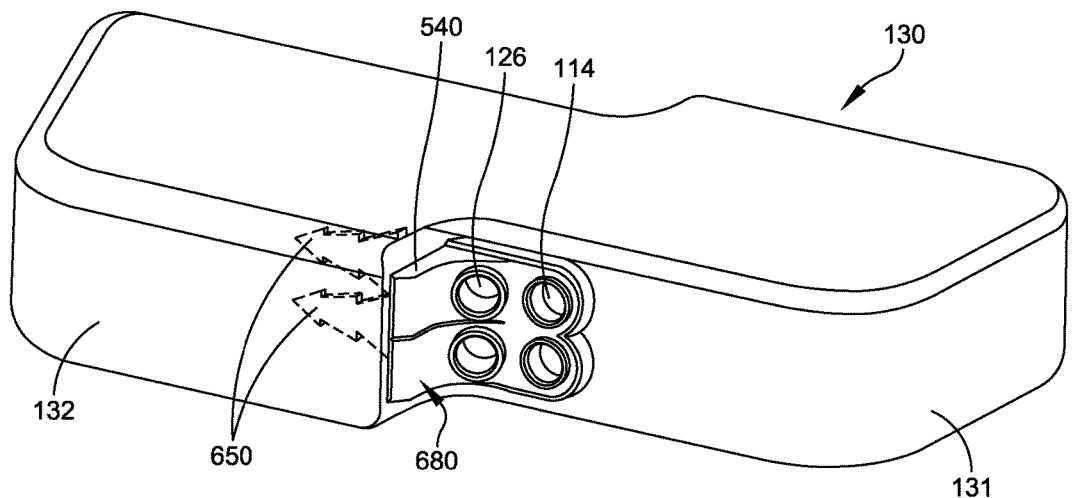
FIG. 9B is a perspective view showing a double-wide version of the implant of FIG. 9A, inserted into the calcaneus.
Figure 9C:
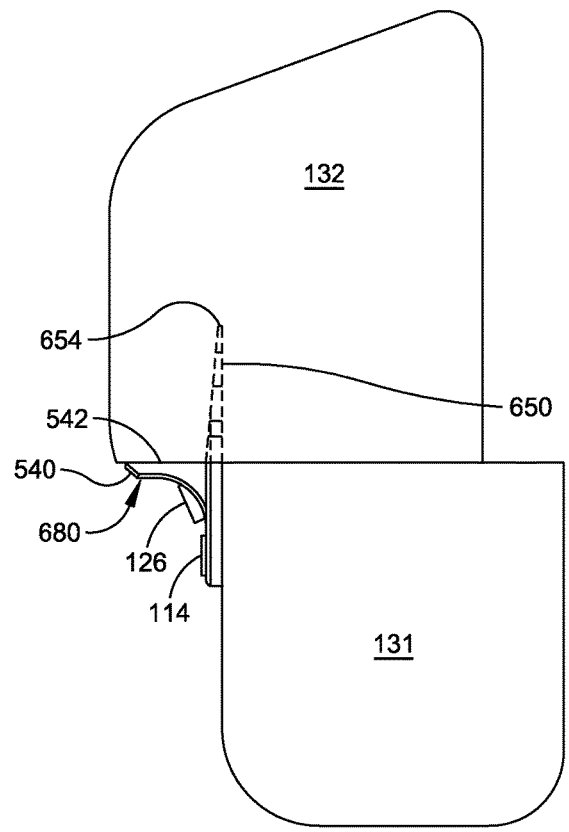
FIG. 9C is a side elevational view of the a double-wide version of the implant of FIGS. 9A and 9B, inserted into the calcaneus.

FIGS. 9B and 9C show an implant 680, which is a double-wide version of the implant 600 of FIG. 9A. The insertion members 650 of implant 680 or inserted into the anterior calcaneus 132, and the implant is securely fastened to the tuberosity using locking screws (not shown) inserted in holes 114. The non-locking screws (not shown) are inserted into the anterior calcaneus, through the holes 126, to provide compression between the tuberosity 131 and the anterior calcaneus 132.

Figure 10:
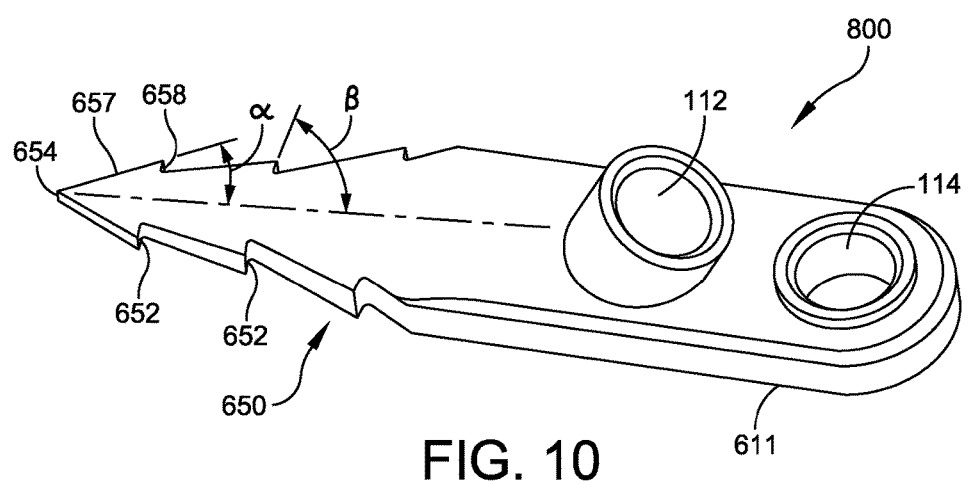
FIG. 10 is a perspective view of a eighth embodiment of an implant.

FIG. 10 shows another embodiment of the invention utilizing an implant 800, which is similar to the implant 600 of FIG. 9A, except that implant 800 does not include wall 540 of implant 600. Implant 800 has at least one insertion member 650 extending beyond wall 540 in an anterior direction, away from elongated plate 510. The at least one insertion member 650 has ridges or barbs 652 on the side edges of insertion member 650. The top face 651 of insertion member 650 is a ramped planar surface. The thickness of insertion member 650 generally decreases toward the anterior end 654 of insertion member 650. The width of insertion member 650 also gradually decreases toward anterior end 654. The insertion member 650 with ridges or barbs 652 is configured to be driven into the cut surface of the anterior calcaneus 132. Each barb 652 has an anterior edge 657 and a posterior edge 658. The anterior edge 657 has a first angle $\alpha$ relative to a longitudinal axis of the implant. The posterior edge 658 has a second angle $\beta$ relative to the longitudinal axis of the implant. The first angle $\alpha$ is smaller than the second angle $\beta$. In some embodiments, the first angle $\alpha$ is less than 50 degrees, and the second angle $\beta$ is less than 90 degrees.

Figure 11:
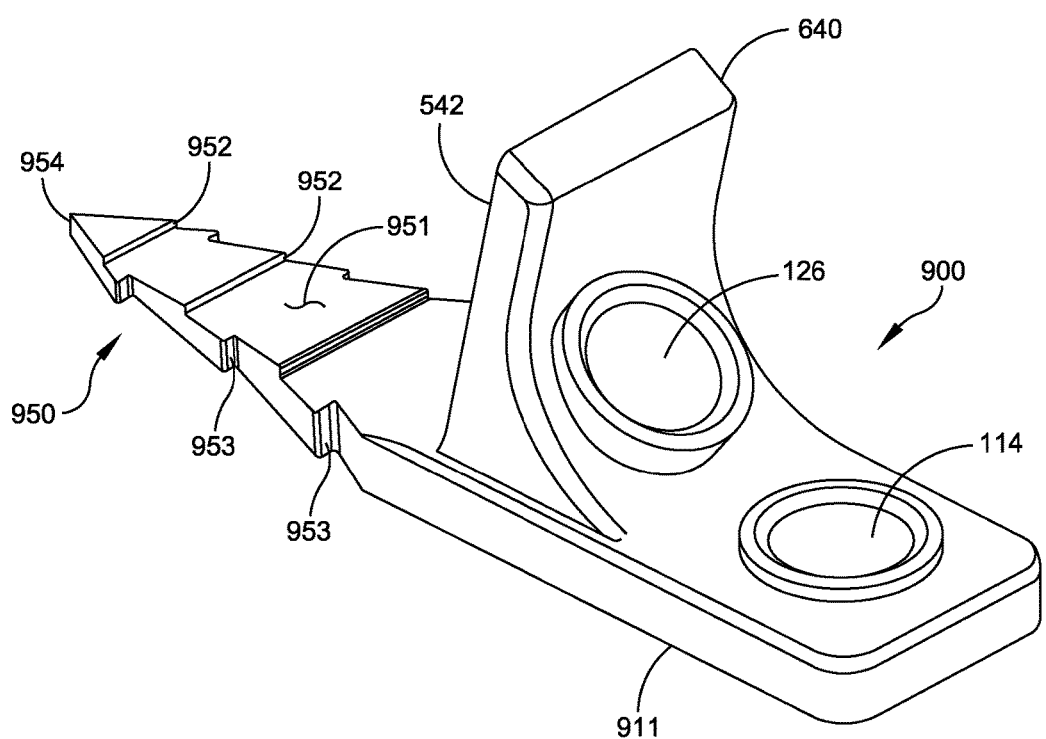
FIG. 11 is a perspective view of a ninth embodiment of an implant.

FIG. 11 shows another embodiment of the invention utilizing an implant 900, which is similar to the implant 600 of FIG. 9A, except that the at least one insertion member 950 has a top face 951 which includes ridges or barbs 952. The top face 951 is opposite face 911, which abuts the lateral or medial surface of the tuberosity 131. The thickness of the insertion member 950 generally decreases toward anterior end 954 of insertion member 950. Like implant 800, insertion member 950 of implant 900 includes ridges or barbs 953 on its side edges. The insertion member 950 with ridges or barbs 952 and 953 is configured to be driven into the cut surface of the anterior calcaneus 132. The ridges or barbs 952, 953 improve implant 900's resistance to being pulled out from the anterior calcaneus 132.

Figure 12A:
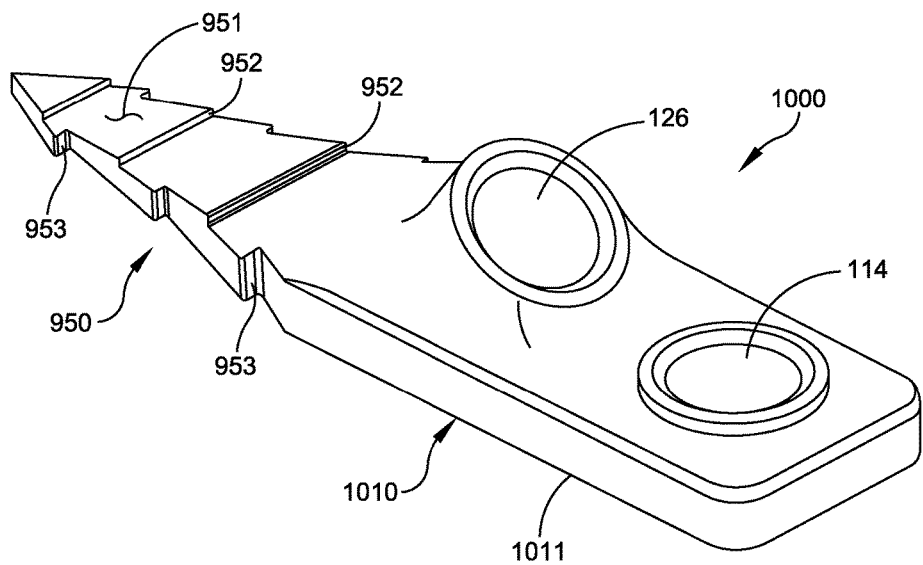
FIG. 12A is a perspective view of a tenth embodiment of an implant.

FIG. 12A shows another embodiment of the invention utilizing an implant 1000, which is similar to the implant 600 of FIG. 11, except that implant 1000 does not include wall 540 of implant 900. Implant 1000 has at least one insertion member 950 extending beyond plate 1010 in an anterior direction. The top face 951 of insertion member 950 has ridges or barbs 952. The at least one insertion member 950 has ridges or barbs 953 on the side edges of the insertion member 950. The thickness of insertion member 950 generally decreases toward anterior end 954. The width of insertion member 950 also gradually decreases toward the anterior end. The insertion member 950 with ridges or barbs 952 is configured to be driven into the cut surface of the anterior calcaneus 132.

Figure 12B:
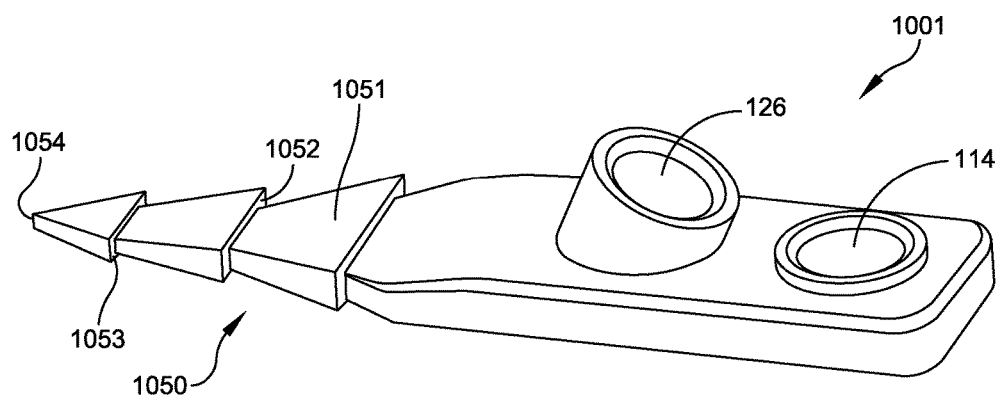
FIG. 12B is a perspective view of an eleventh embodiment of an implant.

FIG. 12B shows another embodiment of the invention utilizing an implant 1001. Implant 1001 has at least one insertion member 1050 extending beyond plate 1003 in an anterior direction. The top face 1051 of insertion member 1050 includes ridges or barbs 952. The at least one insertion member 1050 has barbs 1053 on the side edges of the insertion member 1050. The thickness of insertion member 1050 generally decreases toward anterior end 1054 of insertion member 1050. The width of the insertion member 1050 also gradually decreases toward anterior end 1054. Thus, implant 1001 is similar to the implant 1000 of FIG. 12A, except that the side edges have barbs 1053 aligned with the ridges 1052 on the top face 1051 of the implant.

Figure 13:
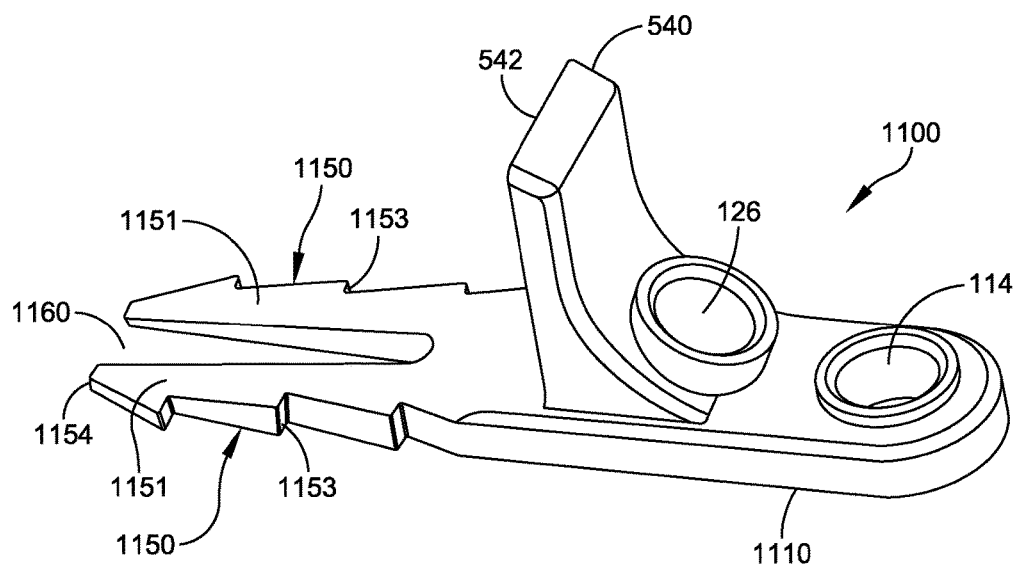
FIG. 13 is a perspective view of a twelfth embodiment of an implant.

FIG. 13 shows another embodiment of the invention utilizing an implant 1100, having at least two insertion members 1150 extending beyond wall 540 in an anterior direction, away from the elongated plate 1110. The insertion members 1150 are separated from each other by at least one slot 1160. The at least two insertion members 1150 each have ridges or barbs 1152 on their outer side edges. The barbs 1152 face outwardly, away from an axis of symmetry of implant 1100. In some embodiments, inside edges 1161 of insertion members 1160 are smooth. In other embodiments (not shown), the inside edges of insertion members 1160 are barbed. The top face 1151 of insertion member 1150 is a ramped planar surface. The thickness of insertion member 1150 generally decreases towards the anterior end 1154 of insertion member 1150. The width of insertion member 1150 also gradually decreases toward its anterior end. The insertion member 1150 with ridges or barbs 1152 is configured to be driven into the cut surface of the anterior calcaneus 132. The ridges or barbs 1152 allow implant 1100 to provide additional resistance to pulling out from the anterior calcaneus 132. The posterior portion of the implant 1100, extending from wall 540 to locking screw hole 114 can be the same as discussed above with reference to implant 500 (FIG. 7), and descriptions of the individual structures are not repeated here.

Figure 14:
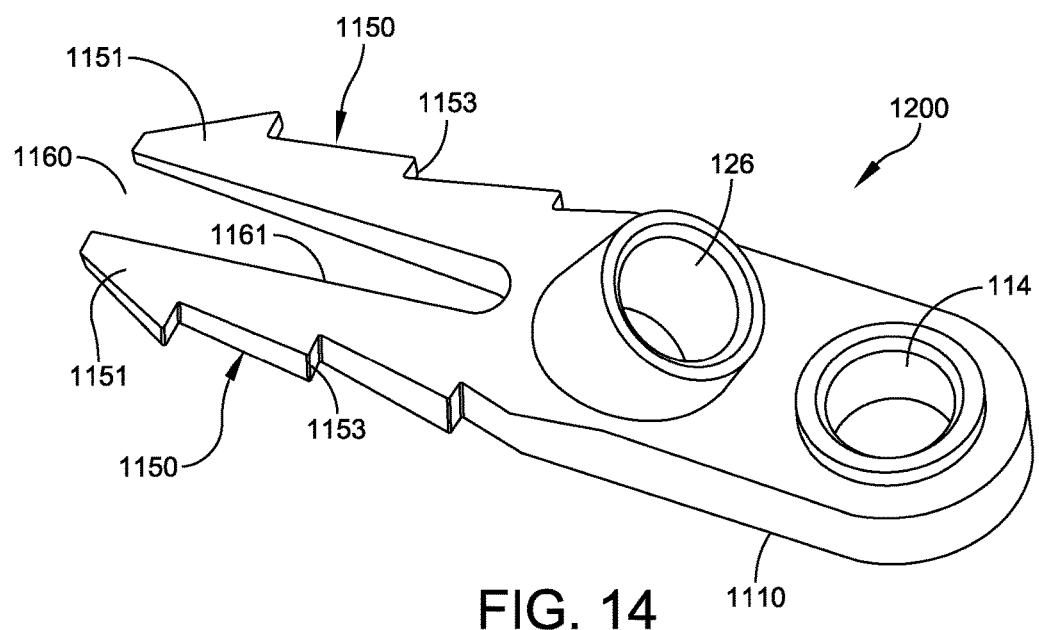
FIG. 14 is a perspective view of a thirteenth embodiment of an implant.

FIG. 14 shows another embodiment of the invention utilizing an implant 1200, which is similar to the implant 1100 of FIG. 13, except that implant 1200 does not include wall 540 of implant 900. The implant 1200 can be the same as implant 1100 of FIG. 13 in all other respects.

Figure 15:
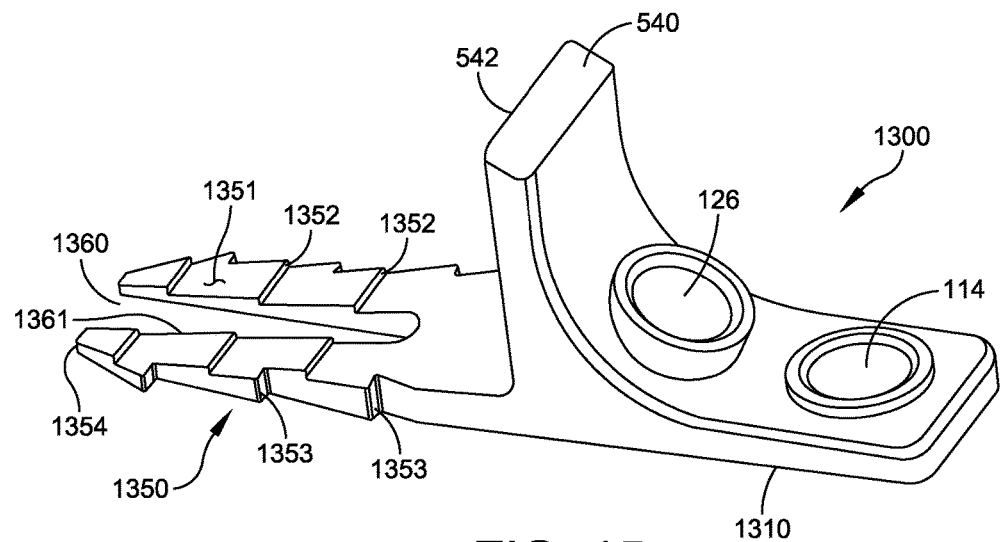
FIG. 15 is a perspective view of a fourteenth embodiment of an implant.

FIG. 15 shows another embodiment of the invention utilizing an implant 1300, having at least two insertion members 1350 extending beyond wall 540 in an anterior direction, away from elongated plate 1310. The insertion members 1350 are separated from each other by at least one slot 1360. The at least two insertion members 1350 have ridges or barbs 1353 on the outer side edges of insertion member 1350 that face outwardly, away from an axis of symmetry of the implant 1300. In some embodiments, the inside edges 1361 of insertion members 1360 are smooth. In other embodiments (not shown), the inside edges of insertion members 1360 are barbed. The top face 1351 of insertion members 1350 has ridges or barbs 1352 extending upwardly, away from a plane containing the first major face 1311 of the implant. The thickness of insertion members 1350 generally decreases toward anterior end 1354 of insertion members 1350. The width of insertion members 1350 also gradually decreases toward its anterior end. The insertion members 1350 with ridges or barbs 1352 and 1353 are configured to be driven into the cut surface of the anterior calcaneus 132. The ridges or barbs 1352, 1353 allow implant 1300 to provide additional resistance to pulling out from the anterior calcaneus 132. The posterior portion of the implant 1300, extending from the wall 540 to the locking screw hole 114 can be the same as discussed above with reference to implant 500 (FIG. 7), and descriptions of the individual structures are not repeated here.

Figure 16:
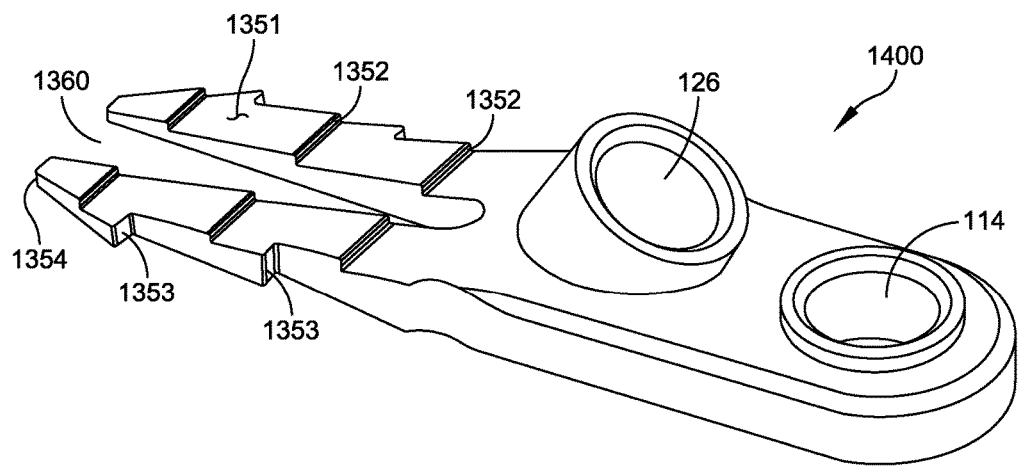
FIG. 16 is a perspective view of a fifteenth embodiment of an implant.

FIG. 16 shows another embodiment of the invention utilizing an implant 1400, which is similar to the implant 1300 of FIG. 15, except that implant 1400 does not include wall 540 of implant 1300. The implant 1400 can be the same as implant 1300 of FIG. 15 in all other respects.

Figure 17:
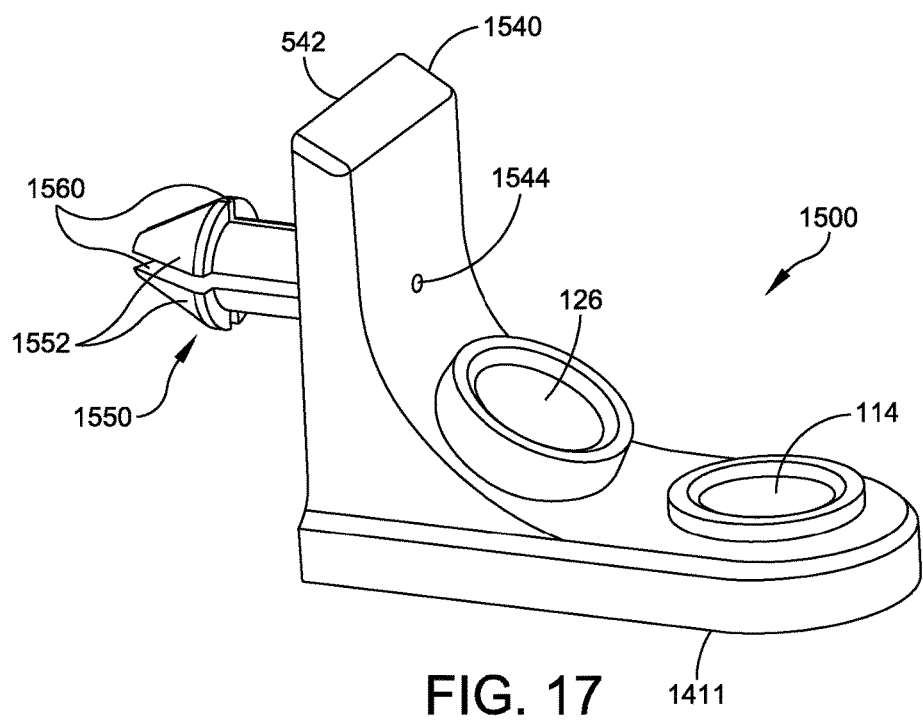
FIG. 17 is a perspective view of a sixteenth embodiment of an implant.

FIG. 17 shows an embodiment of the invention utilizing an implant 1500 having a major face 1411 for interfacing with the medial or lateral surface of the tuberosity 131. A locking screw hole 114 and a non-locking screw 126 are provided. The implant 1500 has an anterior wall 1540 that is similar in function to anterior wall 540 of implant 500, and provides a stop to limit the insertion depth of implant 1500 into anterior calcaneus 132. The anterior wall 542 of anterior wall 1540 has an expanding anchor punch 1550 extending in the anterior direction. In some embodiments, expanding anchor punch 1550 has slots 1560 in the vertical and horizontal planes, dividing punch 1550 into four quadrants. The anterior wall 150 has a pin drive hole 1544, which penetrates the wall 1540 and extends through to the intersection of the two slots. After anchor punch 1550 is driven into anterior calcaneus 132, a pin (not shown) is inserted into pin-drive-hole 1544 to expand the anchor punch 1550 by bending the four quadrants outward. Although anchor punch 1550 has four sections, in other embodiments, the anchor punch may include fewer or more than four separately bendable cantilevered segments with a head for retaining the anchor punch within the bone. Also, hole 1544 can serve to positively position and seat a tool for driving implant 1500 into bone. The configuration of an implant having at least one anchor punch can be varied as would be understood by those skilled in the art.

Figure 18:
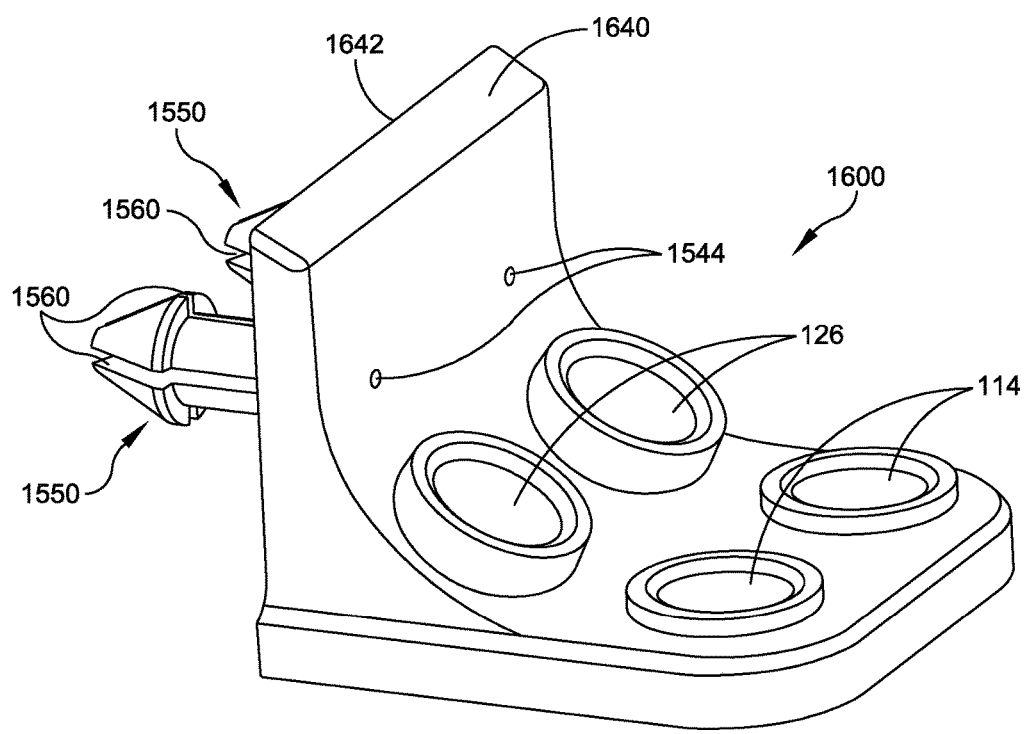
FIG. 18 is a perspective view of a seventeenth embodiment of an implant.

FIG. 18 shows another example of the invention utilizing an implant 1600 having at least one anchor punch 1550. The implant 1600 has all the features of implant 1500 replicated symmetrically about the anterior-posterior axis. The implant 1600 has two rows of holes, including two locking screw holes 114 and two non-locking screw holes 126. Two anchor punches 1550 are included, with two pin-drive-holes 1544. Each of these components in implant 1600 performs the same function as in the implant 1500.

The embodiments described above are only examples. One of ordinary skill can readily configure an implant in accordance with the teachings as described above, with a variety of hole configurations, ridge and/or barb configurations, with or without an a stop wall.

Figure 19:
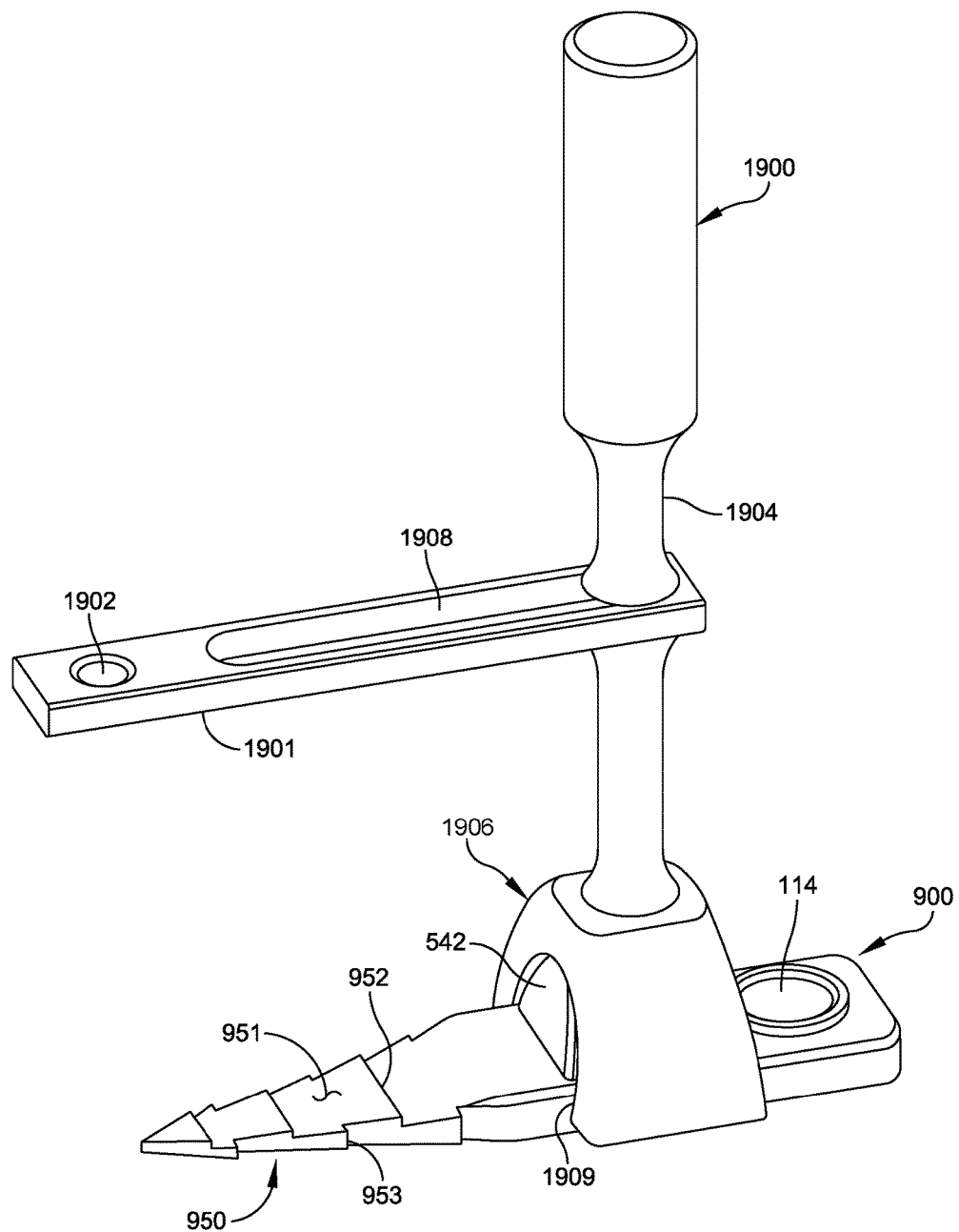
FIG. 19 is a perspective view of a tool for installing the implant.

FIG. 19 shows a tool 1900 and method for inserting one of the example implants 900 of FIG. 11. The same tool 1900 or similar tool may be used to insert any of the single wide implants shown in FIG. 1-3 or 7-17. Further, a similar tool with a wider set of jaws may be used for inserting any of the double wide implants of FIG. 5, 6 or 18. To insert implant 900, bone 130 is first cut. The implant 900 is placed in a tool 1900, shown in FIG. 19. The tool 1900 has a shelf 1901 which is temporarily fastened to the anterior calcaneus 132 by a pin or screw (not shown), inserted through hole 1902. The tool 1900 has a shaft 1904 which engages shelf 1901, and a pair of arms 1906 at the end of shaft 1904, for holding implant 900 during insertion. In some embodiments, shaft 1904 is slidable in the anterior direction along a slot 1908 with respect to shelf 1901 during insertion, and arms 1906 firmly clamp the implant 900. The arms 1906 have an adjustable clamping mechanism (not shown) to permit tightening, for example by a thumbscrew or knob, or a latch to adjust the clamping force on implant 900. Of course, slot 1908 may be omitted, with shaft 1904 having a fixed anterior displacement relative to shelf 1901. The arms 1906 define grooves 1909 for slidably receiving implant 1900, as the implant is driven into bone 132, so that implant 900 is restricted to move in the anterior direction while being driven into the bone.

In some embodiments, where the anterior calcaneus 132 is shifted laterally or medially, implant 900 is driven into the cut face of the anterior calcaneus 132 until anterior surface 542 of wall 540 abuts the bone, implant 900 is placed on the lateral or medial surface of the tuberosity 131, a locking screw is inserted through hole 114 into the tuberosity, and a non-locking screw is inserted through hole 126, into the cut surface of the anterior calcaneus.

In various embodiments, a method for installing the implant comprises: (a) fastening an implant to a first portion of a bone, so that a face of the implant abuts the bone, the implant having a hole configured to receive a fastener oriented at an obtuse angle relative to the face, the implant having a flat surface normal to the face; (b) cutting the bone along a plane of the flat surface, so as to separate a second portion of the bone from the first portion of the bone; (c) offsetting the second portion of the bone relative to the first portion of the bone, such that the flat surface of the implant abuts the second portion of the bone; and (d) fastening the implant to the second portion of the bone using the fastener. In some embodiments (e.g., to install the implant 100 of FIG. 3), steps (a) to (d) are performed in that order. In other embodiments, the steps are performed in a different sequence.

In other embodiments, a method for installing the implant comprises: (a) cutting the bone along a plane of the flat surface, so as to separate a second portion of the bone from the first portion of the bone; (b) offsetting the second portion of the bone relative to the first portion of the bone, such that the flat surface of the implant abuts the second portion of the bone; (c) inserting an insertion member of the implant into a cut surface of the bone until a stop wall of the implant abuts the cut surface, and (d) fastening the implant to the first portion of a bone, so that a face of the implant abuts the bone. In some embodiments (e.g., to install the implant 100 of FIG. 3), steps (a) to (d) are performed in that order. In other embodiments, the steps are performed in a different sequence.

Although the examples are described with reference to an exemplary use for a calcaneal osteotomy, one of ordinary skill can apply the implants and methods described herein to treat other bones. Also, even though the subject matter has been described in terms of exemplary embodiments, it is not limited thereto. Rather, the appended claims should be construed broadly to include other variants and embodiments which may be obvious to those skilled in the art.

What is claimed is:

1. An implant, comprising:
an elongated plate formed of a single piece of material having a first major face and at least one locking screw hole, to receive a locking fastener oriented normal to the major face,
the elongated plate having a wall having a single flat surface normal to the first major face and extending over an entirety of the wall, the flat surface facing away from the at least one locking screw hole, the flat surface free of protrusions,
the wall having a concave fillet located interior to a right angle between the flat surface and the first major face, the concave fillet facing away from the first major face and the flat surface, the concave fillet having a non-locking screw hole between the locking screw hole and the wall, the non-locking screw hole configured to receive a non-locking fastener oriented at an acute angle relative to the locking fastener; and
at least one insertion member extending beyond the wall in an anterior direction, away from the elongated plate, the at least one insertion member having a planar surface continuous and coplanar with the first major face, the at least one insertion member having an edge with barbs, the insertion member configured to be completely inserted into a cut bone, with the entire flat surface contacting a cut surface of the cut bone.

2. The implant of claim 1, wherein each barb has an anterior edge and a posterior edge, the anterior edge having a first angle relative to a longitudinal axis of the implant, the posterior edge having a second angle relative to the longitudinal axis, the first angle being smaller than the second angle.

3. The implant of claim 1, wherein the at least one insertion member has a plurality of edges, each of the plurality of edges having barbs.

4. The implant of claim 1, wherein the at least one insertion member includes two insertion members, with a slot therebetween.

5. The implant of claim 4, wherein each of the two insertion members has the respective edge with barbs thereof facing outwardly, away from an axis of symmetry of the implant.

6. The implant of claim 5, wherein each of the two insertion members further includes a respective face with barbs extending upwardly, away from a plane containing the first major face of the implant.

7. The implant of claim 1, wherein:
the single flat surface extends from a medial edge of the wall to a lateral edge of the wall,
the at least one insertion member has a flat side coplanar with the first major face of the elongated plate, and
the insertion member has at least one ridge on a top surface opposite the flat side.

8. The implant of claim 7, wherein each barb has an anterior edge and a posterior edge, the anterior edge having a first angle relative to a longitudinal axis of the implant, the posterior edge having a second angle relative to the longitudinal axis, the first angle being smaller than the second angle.

9. The implant of claim 8, wherein the at least one insertion member has a plurality of edges, each of the plurality of edges having barbs.

10. The implant of claim 8, wherein the at least one insertion member includes two insertion members, with a slot therebetween.

11. The implant of claim 10, wherein each of the two insertion members has the respective edge with barbs thereof facing outwardly, away from an axis of symmetry of the implant.

12. The implant of claim 11, wherein each of the two insertion members further includes a respective face with barbs facing upwardly, away from a plane containing the first major face of the implant.

* * * * *